(12) United States Patent
Li-Tsang

(10) Patent No.: US 8,386,065 B2
(45) Date of Patent: Feb. 26, 2013

(54) METHOD FOR MANUFACTURING SMART PRESSURE MONITORED SUITS

(75) Inventor: Wai Ping Cecilia Li-Tsang, Hong Kong (CN)

(73) Assignee: The Hong Kong Polytechnic University, Kowloon (CN)

( * ) Notice: Subject to any disclaimer, the term of this patent is extended or adjusted under 35 U.S.C. 154(b) by 1067 days.

(21) Appl. No.: 12/341,499

(22) Filed: Dec. 22, 2008

(65) Prior Publication Data

US 2009/0165688 A1   Jul. 2, 2009

(30) Foreign Application Priority Data

Dec. 27, 2007   (CN) .......................... 2007 1 0308105

(51) Int. Cl.
*G06F 19/00*   (2011.01)
(52) U.S. Cl. ...................................................... 700/132
(58) Field of Classification Search ........... 700/130–133
See application file for complete search history.

(56) References Cited

U.S. PATENT DOCUMENTS

| | | | |
|---|---|---|---|
| 4,527,402 A * | 7/1985 | Swallow et al. | 66/55 |
| 7,043,329 B2 * | 5/2006 | Dias et al. | 700/141 |
| 2005/0049741 A1 * | 3/2005 | Dias et al. | 700/141 |
| 2007/0198118 A1 * | 8/2007 | Lind | 700/138 |
| 2009/0222127 A1 * | 9/2009 | Lind | 700/132 |

FOREIGN PATENT DOCUMENTS

GB            2247826 A  *  3/1992

* cited by examiner

*Primary Examiner* — Nathan Durham
(74) *Attorney, Agent, or Firm* — Foley & Lardner LLP

(57) ABSTRACT

A method for manufacturing smart pressure suits, comprises steps of: measuring physical properties of lycra materials and select a lycra material suitable for making the smart pressure monitored suits; measuring body contour data of a patient and computing a pressure value applied to a disease's part of the patient; inputting the body contour data into a computer and creating a pattern of the smart pressure monitored suits by the body contour data and the pressure value processed by a drawing process module in the computer; plotting a blueprint of the smart pressure monitored suits with a plotter controlled by the computer; and sewing the smart pressure monitored suits according to the selected lycra material and the blueprint. Said method makes whole manufacturing process shorten and the manufactured smart pressure monitored suits has advantages of aesthetic, comfort, good air permeability, less deformation after it is wore in a period of time.

8 Claims, 2 Drawing Sheets

METHOD FOR MANUFACTURING SMART PRESSURE MONITORED SUITS

CROSS-REFERENCE TO RELATED APPLICATION

This application is based upon and claims priority to Chinese Patent Application No. 200710308105.3 filed on Dec. 27, 2007, which application is expressly incorporated herein by reference.

BACKGROUND OF THE INVENTION

1. Field of the Invention

The present invention relates a method for manufacturing pressure monitored suits.

2. Description of Related Art

Pressure therapy has been proved to be one of effective methods in management of hypertrophic scar in medical field. Pressure garments, which is wore by a patent, applies pressure force to a disease's part of the patient, reducing blood supply in the blood vessels of scar tissue, so that it results in local hypoxia at the disease's part, and restrains the growth of scar. Meanwhile, Pressure garments can accelerate the period of reshaping scar, accelerate dissolution of fibrous scar, slow down the growth of scar fibre cell, and speed up the normalization of scar arrangement. If patients wear pressure garments everyday during the preliminary time of treatment, the effect of scar therapy can be better.

Pressure garments in the prior art is made of lycra material, generally by occupational therapy department according to patients' contour data. But the method making pressure garments in the prior art has the following disadvantages of: 1. The pressure garments has weak air permeability, so a patient with the pressure garments feel discomfortable and inconvenient, especially in the summer, the pressure garment may make a patient to sweat, it may be impossible for the patient to complete a full course of treatment; 2. The pressure garments wore for a period of time is easily deformed, so that the pressure applied to a disease's part of a patient can not meet the needs of treatment; and 3. The overall manufacturing procedure is complicated and requires a longer time, and the manufactured pressure garments lack aesthetic.

BRIEF SUMMARY OF THE INVENTION

An object of the present invention is to provide a method for manufacturing smart pressure monitored suits (SPMS), which is quite simple and convenient and has less manufacturing time.

Another object of the present invention is to provide a method for manufacturing smart pressure monitored suits, said smart pressure monitored suits made by said method is comfortable to wear and not easily deformed.

To achieve the above objects, the present invention provides a method for manufacturing smart pressure suits, comprising steps of: S1 measuring physical properties of lycra materials and select a lycra material suitable for making the smart pressure monitored suits; S2: measuring body contour data of a patient and computing a pressure value applied to a disease's part of the patient; S3: inputting the body contour data into a computer, and creating a pattern of the smart pressure monitored suits according to the body contour data and the pressure value processed by a drawing process module in the computer; S4: plotting a blueprint of the smart pressure monitored suits with a plotter controlled by the computer; and S5: sewing the smart pressure monitored suits according to the selected lycra material and the blueprint.

In said method of the present invention, preferably, the step S5 further comprises a step of coating a smooth coating on the lycra material.

In said method of the present invention, preferably, in the step S1, the lycra material is selected by measuring air permeability, colorfastness, dimensional changes after laundering, elongation, and tension of the lycra materials.

In said method of the present invention, preferably, the said method further comprises a step of measuring an actual pressure value applied to the disease's part of the patient by the smart pressure monitored suits, and disposing a padding inside the smart pressure monitored suits if necessary, after the step S5.

In said method of the present invention, preferably, the padding is disposed on a concave of the disease's part of the patient.

In said method of the present invention, preferably, in the step of S5, the smart pressure monitored suits are sewed as clothing of gloves, leg tubes, pants, jackets or pressure coat.

In said method of the present invention, preferably, in the step S1, the pressure value applied to the disease's part body of the patients is reduced by less than 10% in one month's use of the smart pressure monitored suits made of the selected lycra material.

Compared with the prior art, the smart pressure monitored suits manufactured by the method of the present invention has advantages of aesthetic, comfort, good air permeability, less deformation after it is wore in a period of time, and the method of present invention make the whole process of manufacturing the smart pressure monitored suits shorten.

DETAILED DESCRIPTION OF THE INVENTION

In order to further explain the principle and the structure of the present invention, preferred embodiments will be described in details with reference to the drawings hereinafter. However, it is understood that the embodiments are only used to describe and explain the present invention, not to limit the scope of the present invention.

Figure 1:
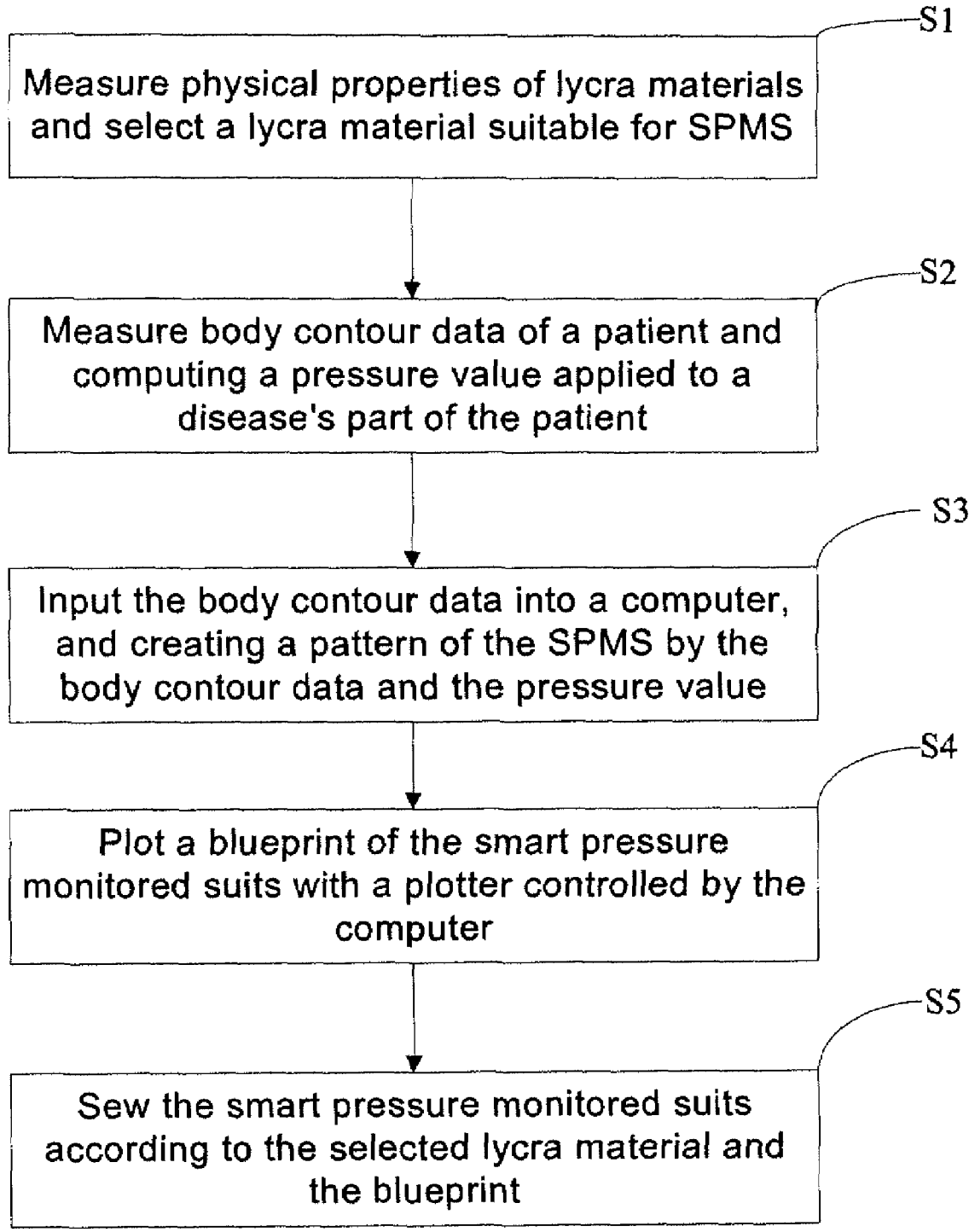
FIG. 1 is a flow chart showing a method for manufacturing smart pressure monitored suits according to a first embodiment of the present invention.

As shown in FIG. 1, a method for manufacturing smart pressure monitored suits according to a first preferred embodiment of the present invention comprises five steps of S1, S2, S3, S4, and S5:

S1: measuring physical properties of lycra materials and selecting a lycra material suitable for making the smart pressure monitored suits.

S2: measuring body contour data of a patient and computing a pressure value applied to a disease's part of the patient. Herein, an operator may collect the body contour data of the patient with various auxiliary equipments in the prior art, and compute the pressure value applied to the disease's part of the patient, such as scar, according to the body contour data and the demand of treatment.

S3: inputting the body contour data into a computer, and creating a pattern of the smart pressure monitored suits by the body contour data and the pressure value processed by a drawing process module in the computer. Herein, the drawing process module in the computer storages a procedure for creating the pattern of the smart pressure monitored suits in advance, may automatically process the body contour data and the pressure value inputted, and automatically create a pattern of smart pressure monitored suits meeting the requirements according to processed results.

S4: plotting a blueprint of the smart pressure monitored suits with a plotter controlled by the computer. Specifically, after the pattern of the smart pressure monitored suits is automatically created, the plotter, which is connected with the computer, is controlled by the computer to plot a blueprint of the smart pressure monitored suits.

S5: sewing the smart pressure monitored suits with the selected lycra material according to the blueprint.

In order to reduce the friction between the smart pressure monitored suits and the body surface of the patient and improve the wearing comfort degree, in the step of S5, a smooth coating may be coated on the lycra material.

In the step S1, the lycra material may be selected by measuring air permeability, colorfastness, dimensional changes after laundering, elongation, and tension of lycra materials.

In order to keep the pressure applied to a disease's part of the patient constant, the pressure value applied to the disease's part body of the patients is reduced by less than 10% in one month's use of the smart pressure monitored suits made from the selected lycra material.

Figure 2:
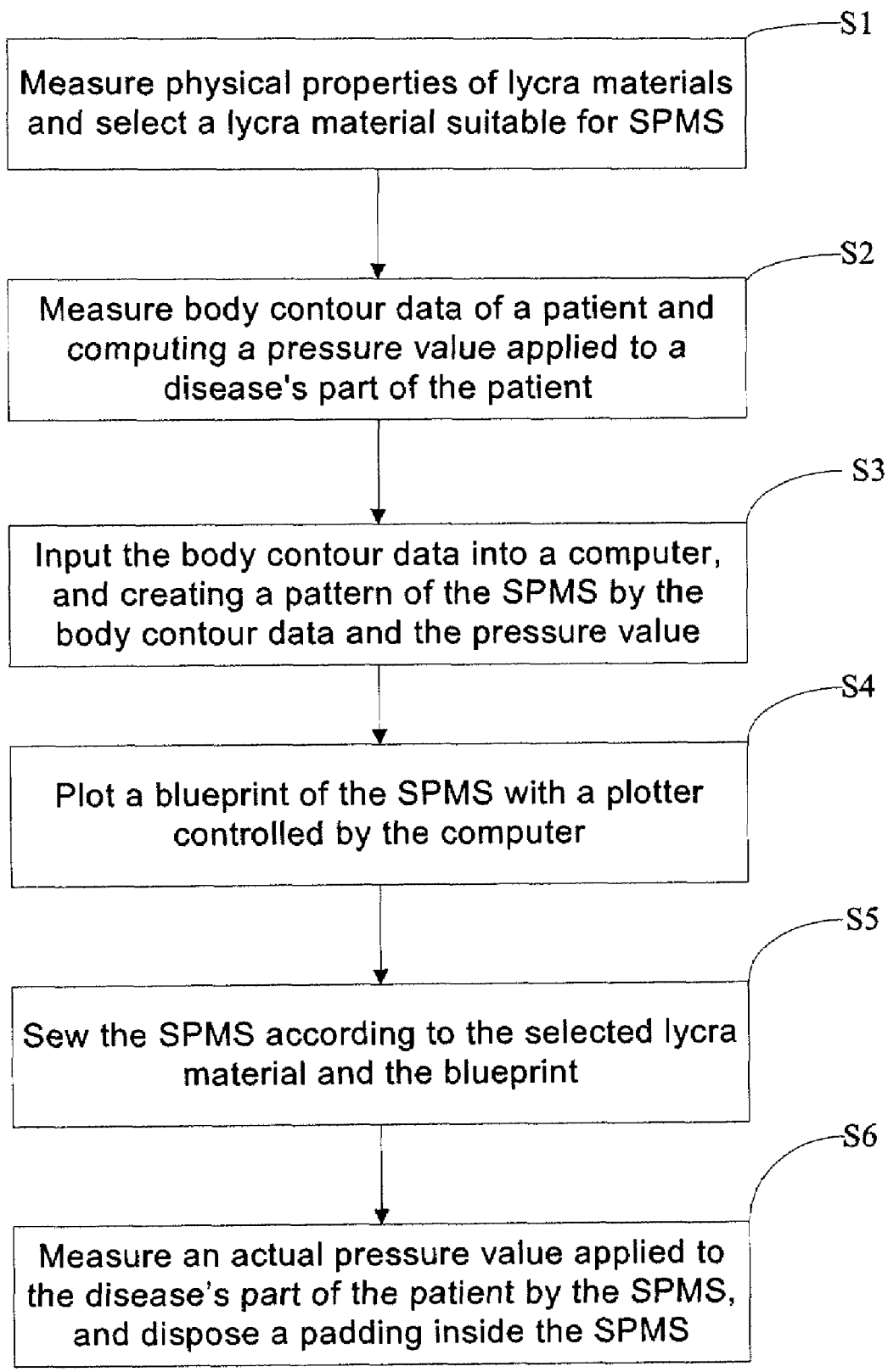
FIG. 2 is a flow chart showing a method for manufacturing smart pressure monitored suits according to a second embodiment of the present invention.

As shown in FIG. 2, a method for manufacturing smart pressure suits according to the second embodiment of the invention comprises six steps of S1, S2, S3, S4, S5, and S6.

Compared to the first embodiment, the second embodiment of the present invention further includes a step of adjusting the smart pressure monitored suits besides the leading five steps as those in the first embodiment.

According to step S6, in order to improve treatment effect, an actual pressure value applied to the disease's part of the patient is measured after the patient wears the smart pressure monitored suits, and a padding may be disposed inside the smart pressure monitored suits according to the actual pressure value measured if necessary.

Preferably, the padding is disposed on a concave of the disease's part of the patient. Since a pressure in the concave of the disease's part may be less than a pressure of treatment due to the concave of the disease's part of the patent, it is required that a padding is disposed on the concave of the disease's part, so as to transfer a pressure of the smart pressure monitored suits to the concave of the disease's part.

In the step S5, the smart pressure monitored suits of the present invention may be sewed as clothing of gloves, leg tubes, pants, jackets or pressure coat as required.

The smart pressure monitor suits of the present invention may be applied in various medical conditions, such as post burn scar pressure management, varicose vein, deep vein thrombosis, post surgical mastectomy, odema management and other sports or orthopaedic cases management.

What is claimed is:

1. A method for manufacturing a smart pressure monitored suit, comprising:
   measuring physical properties of lycra materials to select a lycra material suitable for making the smart pressure monitored suit, wherein the lycra material is selected by measuring air permeability, colorfastness, dimensional changes after laundering, elongation, and tension of the lycra materials;
   measuring body contour data of a patient and computing a pressure value applied to a diseased part of the patient according to the measured body contour data and the patient's demand of treatment;
   inputting the body contour data into a computer, and creating a pattern of the smart pressure monitored suit by the body contour data and the pressure value processed by a drawing process module in the computer;
   plotting a blueprint of the smart pressure monitored suit with a plotter controlled by the computer; and
   sewing the smart pressure monitored suit according to the selected lycra material and the blueprint.

2. The method according to claim 1, wherein the step of sewing the smart pressure monitored suit according to the selected lycra material and the blueprint further comprises a step of coating further comprising forming a smooth coating on the lycra material.

3. The method according to claim 2, further comprising: measuring an actual pressure value applied to the diseased part of the patient by the smart pressure monitored suit, and disposing a padding inside the smart pressure monitored suits if necessary, after the step of sewing the smart pressure monitored suit according to the selected lycra material and the blueprint.

4. The method according to claim 3, wherein the padding is disposed on a concave of the diseased part of the patient.

5. The method according to claim 2, wherein in the step of sewing the smart pressure monitored suit according to the selected lycra material and the blueprint, the smart pressure monitored suit is sewed as clothing of a glove, a let tube, pants, a jacket, or a pressure coat.

6. The method according to claim 1, further comprising: measuring an actual pressure value applied to the diseased part of the patient by the smart pressure monitored suit, and disposing a padding inside the smart pressure monitored suit if necessary, after the step of sewing the smart pressure monitored suit according to the selected lycra material and the blueprint.

7. The method according to claim 6, wherein the padding is disposed on a concave of the diseased part of the patient.

8. The method according to claim 1, wherein in the step of sewing the smart pressure monitored suit according to the selected lycra material and the blueprint, the smart pressure monitored suit is sewed as clothing of a glove, a let tube, pants, a jacket, or a pressure coat.

* * * * *